(12) United States Patent
Kikusawa

(10) Patent No.: US 7,500,842 B2
(45) Date of Patent: Mar. 10, 2009

(54) CATHETER MOLDING APPARATUS

(75) Inventor: Yoshiharu Kikusawa, Suita (JP)

(73) Assignee: PLA Giken Co., Ltd., Osaka (JP)

( * ) Notice: Subject to any disclaimer, the term of this patent is extended or adjusted under 35 U.S.C. 154(b) by 18 days.

(21) Appl. No.: 11/597,091

(22) PCT Filed: Jun. 10, 2004

(86) PCT No.: PCT/JP2004/008132

§ 371 (c)(1),
(2), (4) Date: Nov. 20, 2006

(87) PCT Pub. No.: WO2005/120804

PCT Pub. Date: Dec. 22, 2005

(65) Prior Publication Data

US 2007/0243282 A1    Oct. 18, 2007

(51) Int. Cl.
*B29C 47/06* (2006.01)
*B29C 47/20* (2006.01)
(52) U.S. Cl. .................... 425/113; 425/133.1; 425/380; 425/382.4; 425/462
(58) Field of Classification Search ................. 425/113, 425/114, 133.1, 192 R, 380, 382.4, 462, 463
See application file for complete search history.

(56) References Cited

U.S. PATENT DOCUMENTS

| | | | | |
|---|---|---|---|---|
| 2,513,106 A | * | 6/1950 | Prendergast | 156/143 |
| 3,640,659 A | * | 2/1972 | Dimitroff | 156/500 |
| 4,125,585 A | * | 11/1978 | Rosenbaum | 264/171.26 |
| 4,247,504 A | * | 1/1981 | Karppo | 264/171.18 |
| 4,764,324 A | * | 8/1988 | Burnham | 264/103 |
| 5,063,018 A | * | 11/1991 | Fontirroche et al. | 264/514 |
| 5,156,715 A | * | 10/1992 | Starnes, Jr. | 156/500 |

FOREIGN PATENT DOCUMENTS

| | | |
|---|---|---|
| EP | 0747205 A2 | 12/1996 |
| EP | 1344549 A1 | 9/2003 |

(Continued)

OTHER PUBLICATIONS

International Search Report of Application No. PCT/JP2004/008121, Sep. 21, 2004.

*Primary Examiner*—Robert B Davis
*Assistant Examiner*—Joseph Leyson
(74) *Attorney, Agent, or Firm*—Pillsbury Winthrop Shaw Pittman LLP

(57) ABSTRACT

A catheter molding apparatus that includes a fore-stage extrusion molding device for extrusion molding an inner layer tube of resin so as to fit a core wire material of metal therein, a braided layer attaching unit for attaching a braided layer made by the braiding of a reinforcing thread to the outer surface of the inner layer tube molded by the fore-stage extrusion molding device and once cooled, thereby molding a braided tube. The apparatus also includes a post-stage extrusion molding device for extrusion molding a raw material tube for a catheter by fitting an outer layer tube of resin thereon, and a take-off unit for taking off the raw material tube. The fore-stage extrusion molding device, braided layer attaching unit, post-stage extrusion molding device, and take-off unit are continuously disposed along the longitudinal direction of the tubes.

4 Claims, 7 Drawing Sheets

FOREIGN PATENT DOCUMENTS

| | | |
|---|---|---|
| JP | 4-212377 | 8/1992 |
| JP | 05-026381 | 2/1993 |
| JP | 05-162186 | 6/1993 |
| JP | 10-249954 | 9/1998 |
| JP | 2001-88199 | 4/2001 |
| JP | 2001-277330 | 10/2001 |
| JP | 2002-331567 | 11/2002 |
| JP | 2003-251680 | 9/2003 |

* cited by examiner

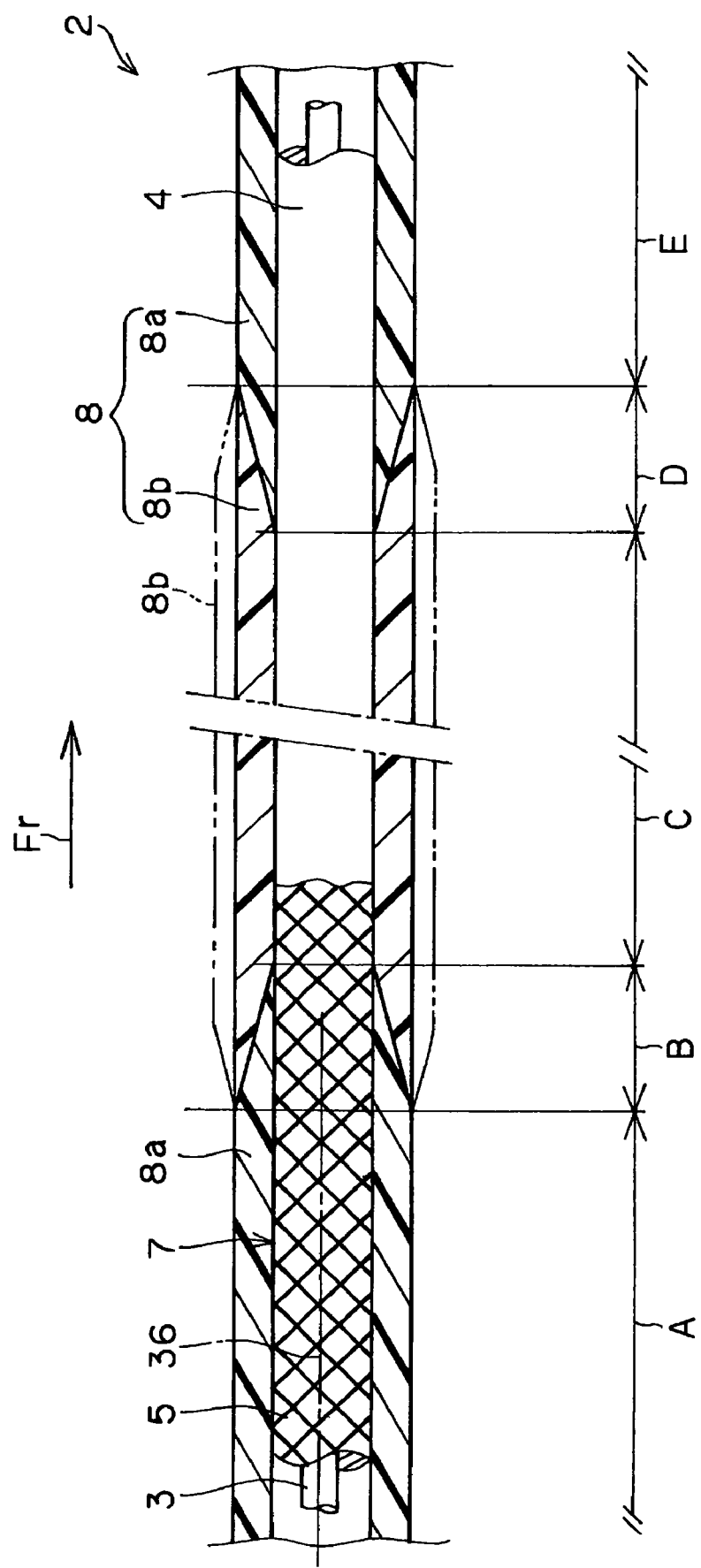

CATHETER MOLDING APPARATUS

CROSS REFERENCE TO RELATED APPLICATIONS

This application is a U.S. National Phase of PCT/JP2004/008132, filed Jun. 10, 2004, which is incorporated herein by reference thereto in its entirety.

TECHNICAL FIELD

The present invention relates to a multi-layer tube molding apparatus, and more particularly it relates to a catheter molding apparatus which makes it possible to mold a raw material tube for a medical catheter tube, which is a multi-layer tube.

BACKGROUND ART

As for the multi-layer tube molding apparatus, there has heretofore been one shown in Patent Document 1 indicated below. The molding apparatus in this official gazette includes first and second extruders for thermally melting and extruding first and second resins, respectively, and first and second dies having molded therein inner and outer layer tube molding passages for passing therethrough the first and second resins extruded from these extruders to enable the molding of inner and outer layer tubes. Further, these first and second dies have first and second inflow passages molded therein. These first and second inflow passages enable the first and second resins extruded by said first and second extruders to flow into said inner and outer layer tube molding passages.

Disposed between said first and second dies is a braided layer attaching unit. This braided layer attaching unit attaches a braided layer, formed by the braiding of a reinforcing thread, to the outer surface of the inner layer tube immediately after the extrusion molding by said first die. Thereby, a braided tube is molded. Next, said second die fits said outer layer tube on said braided tube. Thereby, said multi-layer tube is molded.

Patent Document 1: Japanese Patent Laid-Open Official Gazette No. Hei 10-249954.

DISCLOSURE OF THE INVENTION

Problems to be Solved by the Invention

In this connection, said conventional multi-layer tube molding apparatus has the following problems.

That is, immediately after being extrusion molded, the inner layer tube has been heated, remaining still soft.

Consequently, when the braided layer formed by the braiding of a reinforcing thread is attached to the outer surface of said inner layer tube, as described above, there is a possibility that said reinforcing thread cuts into the outer surface of said inner layer tube to deform the outer surface. Thus, there is a possibility that the error in the outer diameter dimension of said braided tube increases.

Here, as an example of a multi-layer tube, there is a catheter. This catheter is a medical material adapted to be inserted into the body. The outer diameter dimension of this catheter is generally 1.0-1.5 mm, a very small value. Further, since the catheter is inserted into the body, as described above, it is required that said error in the outer diameter dimension be a sufficiently small value as considered from said small outer diameter dimension. That is, particularly high accuracy is required for catheter dimension Consequently, when a catheter is to be molded by using said braided tube, as described above, in the case where the error in the outer diameter dimension of the braided tube is large, it is difficult to improve the dimensional accuracy of said catheter.

Further, in the case where a catheter is to be molded from said multi-layer tube, generally, the wall thickness and outer diameter dimension of the outer layer tube are caused to change at its longitudinal portions, so as to conform to the specifications of this catheter. Such change can be obtained by changing the flow rate per unit time of the resin extruded from said second extruder.

Here, when the flow rate of the resin being extruded from the second extruder is changed, as described above, there occurs a change in the pressure of the resin in said second inflow passage. And, this pressure change tends to cause, though little, the expansion or contraction of the resin in said second inflow passage.

Consequently, when the flow rate of the resin being extruded from the second extruder is changed, said expansion or contraction of the resin causes the flow rate of the resin passing through said outer layer tube molding passage to fail to immediately respond to said flow rate change in the second extruder. That is, there occurs a response delay. As a result, it is not easy to improve the accuracies of the outer layer tube wall-thickness and outer diameter dimension. That is, it is not easy to cause said catheter to meet various specifications Means for Solving Problems The present invention has been accomplished with the above situations in mind. An object of the present invention is to improve the dimensional accuracy of catheters molded by a catheter molding apparatus.

Further, another object of the invention is to ensure that the molding of catheters adapted to improve the dimensional accuracy as described above is achieved with a simple arrangement.

The invention provides an arrangement including a fore-stage extrusion molding device for extrusion molding an inner layer tube of resin so as to fit a core wire material of metal therein, a braided layer attaching unit for attaching a braided layer made by the braiding of a reinforcing thread to the outer surface of the inner layer tube molded by said fore-stage extrusion molding device and once cooled, thereby molding a braided tube, a post-stage extrusion molding device for extrusion molding a raw material tube for a catheter by fitting an outer layer tube of resin thereon, and a take-off unit for taking off said raw material tube, said fore-stage extrusion molding device, braided layer attaching unit, post-stage extrusion molding device, and take-off unit being continuously disposed along the longitudinal direction of said tubes.

In addition, added to said invention, the respective maximum processing speeds of said fore-stage extrusion molding device, post-stage extrusion molding device, and take-off unit may be set to be greater than the maximum processing speed of said braided layer attaching unit.

Further, added to said invention, said post-stage extrusion molding device may include first and second extruders for thermally melting and extruding first and second resins of different kinds, a die having molded therein an inner layer portion molding passage for forwardly passing therethrough said first resin extruded from said first extruder to make it possible to mold the inner layer portion of said outer layer tube and an outer layer portion molding passage for forwardly passing therethrough said second resin extruded from said second extruder to make it possible to mold the outer layer portion of said outer layer tube, and first and second flow regulating valves for making it possible to regulate the respective flow rates per unit time of the first and second resins extruded from said first and second extruders and directed to said inner and outer layer portion molding passages.

Further, added to said invention, the respective valve bodies of said first and second flow regulating valves may be disposed in said die.

Further, added to said invention, the arrangement may be made such that the respective front ends of said inner and outer layer portion molding passages are used as inner and outer extrusion ports, an auxiliary die is installed forwardly of said die, said auxiliary die having an auxiliary die hole molded therein which, at a position forwardly remote from said inner and outer extrusion ports, enables said raw material tube to pass forwardly therethrough, and an imaginary frustoconical sleeve which connects the outer opening edge of said outer extrusion port to the opening edge of said auxiliary die hole has a space molded throughout its outer region in the circumferential direction thereof.

Further, added to said invention, the separation distance dimension from said inner and outer extrusion ports to said auxiliary die hole may be made variable.

Effects of the Invention

The effects of the invention are as follows.

The invention provides an arrangement including a fore-stage extrusion molding device for extrusion molding an inner layer tube of resin so as to fit a core wire material of metal therein, a braided layer attaching unit for attaching a braided layer made by the braiding of a reinforcing thread to the outer surface of the inner layer tube molded by said fore-stage extrusion molding device and once cooled, thereby molding a braided tube, a post-stage extrusion molding device for extrusion molding a raw material tube for a catheter by fitting an outer layer tube of resin thereon, and a take-off unit for taking off said raw material tube, said fore-stage extrusion molding device, braided layer attaching unit, post-stage extrusion molding device, and take-off unit being continuously disposed along the longitudinal direction of said tubes.

Consequently, when said inner layer tube is molded, its outer surface is once cooled, whereby it is cured to some extent. Thus, thereafter, when the braided layer is attached to the outer surface of said inner layer tube, the reinforcing thread of the braided layer is prevented from cutting into the outer surface of said inner layer tube.

As a result, the accuracy of the outer diameter dimension of the braided tube improves. Consequently, when a raw material tube is molded by fitting the outer layer tube on this braided tube, the accuracy of the outer diameter dimension of this raw material tube improves. Thus, the dimensional accuracy of a catheter molded from this raw material tube improves.

Further, as described above, the fore-stage extrusion molding device, braided layer attaching unit, post-stage extrusion molding device, and take-off unit are continuously disposed. Consequently, as compared with the case in which these are individually disposed so as to intermittently mold intermediate molded articles from the raw material tube, the arrangement of the catheter molding apparatus becomes simple. That is, as described above, the molding of a catheter intended to have its dimensional accuracy improved is achieved with a simple arrangement.

In addition, added to said invention, the respective maximum processing speeds of said fore-stage extrusion molding device, post-stage extrusion molding device, and take-off unit may be set to be greater than the maximum processing speed of said braided layer attaching unit.

Here, the improvement in the respective processing speeds of said fore-stage extrusion molding device, post-stage extrusion molding device, and take-off unit can be achieved to some extent with a simple arrangement, for example, by simply increasing the speed of the electric motor. When it is intended to further increase the processing speed of said braided layer attaching unit, however, the centrifugal force in each part rapidly increases, so that the arrangement will become relatively complicated.

So, as described above, the respective maximum processing speeds of said fore-stage extrusion molding device, post-stage extrusion molding device, and take-off unit are set to be greater than the maximum processing speed of said braided layer attaching unit. That is, while the maximum processing speed of said braided layer attaching unit is set at a desired value in such a way as not to make its arrangement excessively complicated, it is arranged that the maximum processing speed of the catheter molding apparatus be not limited by the respective maximum processing speeds of said fore-stage extrusion molding device, post-stage extrusion molding device, and take-off unit. Thereby, the catheter molding apparatus can rationally develop the maximum processing speed with a simple arrangement.

Further, in said invention, said post-stage extrusion molding device may include first and second extruders for thermally melting and extruding first and second resins of different kinds, a die having molded therein an inner layer portion molding passage for forwardly passing therethrough said first resin extruded from said first extruder to make it possible to mold the inner layer portion of said outer layer tube and an outer layer portion molding passage for forwardly passing therethrough said second resin extruded from said second extruder to make it possible to mold the outer layer portion of said outer layer tube, and first and second flow regulating valves for making it possible to regulate the respective flow rates per unit time of the first and second resins extruded from said first and second extruders and directed to said inner and outer layer portion molding passages.

With the arrangement thus made, the molding of the outer layer tube in said raw material tube is achieved by causing the first and second resins extruded by said first and second extruders to pass through said inner and outer portion molding passages. Further, at this time, the respective flow rates of said first and second resins are regulated by the actuation of said first and second flow regulating valves. Thereupon, the respective wall-thicknesses and outer diameter dimensions of the inner and outer layer portions of said outer layer tube can be adjusted to desired values to mold a desired raw material tube.

Here, when said first and second flow regulating valves are actuated, the first and second resins in the "passages" extending from said first and second flow regulating valves to said inner and outer layer portion molding passages are given external forces on the basis of this actuation, and their volumes tend to vary.

However, the volumes of the first and second resins in said "passages" are smaller than said volumes from said first and second extruders to said inner and outer layer portion molding passages. Consequently, as compared with the conventional art devoid of the first and second flow regulating valves, the volumetric changes, with respect to said external forces, of the first and second resins in said "passages" are suppressed to be small.

Thus, the changes in the flow rates of the first and second resins flowing through said inner and outer layer portion molding passages follow the actuation of said first and second flow regulating valves with good response. Consequently, the dimensional accuracy of the outer layer tube of said raw material tube improves. That is, the dimensional accuracy of the catheter improves.

Further, in said invention, the respective valve bodies 45 of said first and second flow regulating valves are disposed in said die.

Consequently, the volumes of the first and second resins in said "passages" extending from the respective bodies disposed in said die to the inner and outer layer portion molding passages formed in said die become smaller. Thus, the volumetric changes, with respect to said external forces, of said first and second resins in said "passages" are suppressed to be smaller.

As a result, the changes in the flow rates of the first and second resins flowing through said inner and outer layer portion molding passages follow the actuation of said first and second flow regulating valves with better response. Consequently, the dimensional accuracy of the outer layer tube of said raw material tube further improves. That is, the dimensional accuracy of the catheter further improves.

Further, in said invention, the arrangement may be made such that the respective front ends of said inner and outer layer portion molding passages are used as inner and outer extrusion ports, an auxiliary die is installed forwardly of said die, said auxiliary die having an auxiliary die hole molded therein which, at a position forwardly remote from said inner and outer extrusion ports, enables said raw material tube to pass forwardly therethrough, and an imaginary frustoconical sleeve which connects the outer opening edge of said outer extrusion port to the opening edge of said auxiliary die hole has a space molded throughout its outer region in the circumferential direction thereof.

With the arrangement thus made, in the molding of said raw material tube, when the outer layer tube is extruded forwardly of the die, the outer surface of this outer layer tube contacts the air in said space, whereby it is cured to some extent. And, immediately after this curing, the outer surface of said raw material tube slides on the inner surface of said auxiliary die hole while making pressure contact therewith. Thereupon, the outer surface of said raw material tube is finished to be a smooth surface. As a result, the dimensional accuracy of the catheter further improves.

Further, in said invention, the separation distance dimension from said inner and outer extrusion ports to said auxiliary die hole may be made variable.

With the arrangement thus made, adjusting said separation distance dimension makes it possible to adjust the time in which the outer surface of the outer layer tube of the raw material tube immediately after being extruded forwardly of said die contacts the air in said space. Thereby, the extent of the curing of the outer surface of said outer layer tube can be set in a more desirable state. And, in that the outer surface of this outer layer tube slide-contacts the inner surface of said auxiliary die hole, the outer surface of the raw material tube is finished to be a smoother surface.

BRIEF DESCRIPTION OF THE DRAWINGS

FIG. 7 is a sectional view showing another embodiment concerning the raw material tube.

DESCRIPTION OF THE REFERENCE CHARACTERS

Figure 1:
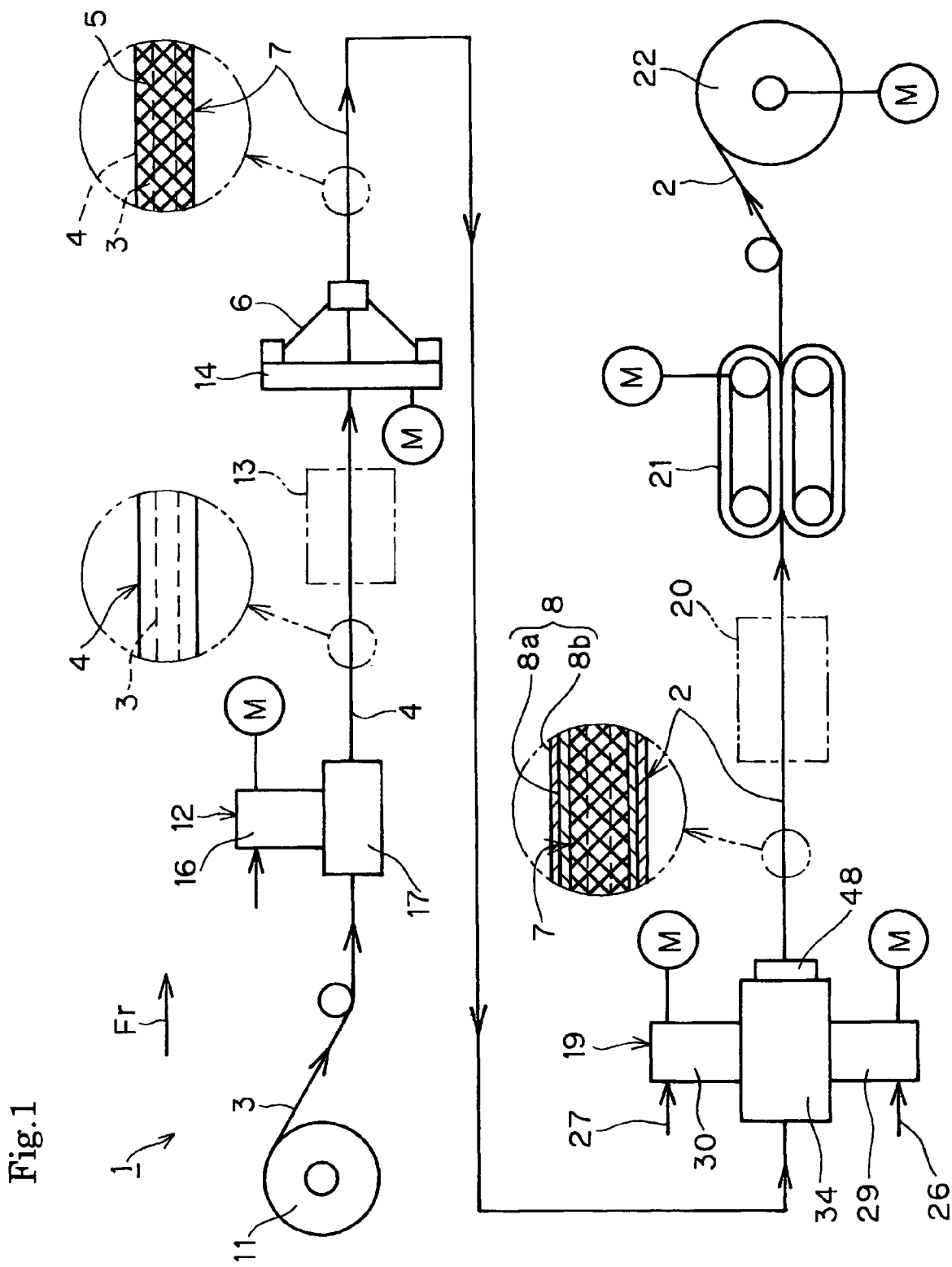
FIG. 1 is an overall sketch of a catheter molding apparatus.

1 Catheter molding apparatus
2 Raw material tube
3 Core wire material
4 Inner layer tube
5 Braided layer
6 Reinforcing thread
7 Braided tube
8 Outer layer tube
12 Fore-stage extrusion molding device
13 Cooling device
14 Braided layer attaching unit
19 Post-stage extrusion molding device
21 Take-off unit
26 First resin
27 Second resin
29 First extruder
30 Second extruder
32 Inner layer portion molding passage
33 Outer layer portion molding passage
34 Die
36 Axis
37 Inner extrusion port
38 Outer extrusion port
40 First inflow passage
41 Second inflow passage
43 First flow regulating valve
45 Valve body
44 Second flow regulating valve
48 Auxiliary die
49 Auxiliary die hole
50 Outer opening edge
51 Opening edge
52 Imaginary frustoconical sleeve
53 Space
56 Inner diameter varying device
D1 Inner diameter dimension
D2 Inner diameter dimension
L Separation distance dimension
Q1 Flow rate
Q2 Flow rate

BEST MODE FOR CARRING OUT THE INVENTION

Concerning the catheter molding apparatus, it is intended to further improve the dimensional accuracy of a catheter molded. Further, in order to realize the object of achieving the molding of a catheter by a simple arrangement, the best mode for carrying out the invention is as follows.

That is, the catheter molding apparatus includes a fore-stage extrusion molding device for extrusion molding an inner layer tube of resin so as to fit a core wire material of metal therein, a braided layer attaching unit for attaching a braided layer made by the braiding of a reinforcing thread to the outer surface of the inner layer tube molded by said fore-stage extrusion molding device and once cooled, thereby molding a braided tube, a post-stage extrusion molding device for extrusion molding a raw material tube for a catheter by fitting an outer layer tube of resin thereon, and a take-off unit for taking off said raw material tube. The fore-stage extrusion molding device, braided layer attaching unit, post-stage extrusion molding device, and take-off unit are continuously disposed along the longitudinal direction of said tubes.

EMBODIMENTS

To described the invention in more detail, embodiments thereof will be described with reference to the accompanying drawings.

In FIG. 1, the reference character 1 denotes a catheter molding apparatus. This catheter molding apparatus 1 is used for molding a raw material tube 2 for medical catheters. Further, the arrow Fr indicates a forward direction of travel during the molding of said raw material tube 2.

Said raw material tube 2 is a multi-layer tube of circular cross section. Said raw material tube 2 includes a core wire material 3 of metal, an inner layer tube 4 of resin having this core wire material 3 fitted therein, and a reinforcing braided layer 5 attached to the outer surface of said inner layer tube 4. Said braided layer 5 is molded by the braiding of a reinforcing thread 6 of thin metal wire. A braided tube 7 is molded by said inner layer tube 4 and braided layer 5. Further, said raw material tube 2 includes an outer layer tube 8 of resin fitted on said braided tube 7. A longitudinal desired portion of said raw material tube 2 is cut to a desired dimension and the core wire material 3 is pulled out of the inner layer tube 4 of this cut raw material tube 2, whereupon said catheter is obtained. The outer diameter of this catheter is about 0.7-10 mm, and the inner diameter is about 0.3-8 mm.

Said catheter molding apparatus 1 includes a winder 11 having said core wire material 3 wound thereon, a fore-stage extrusion molding device 12 for extrusion molding said inner layer tube 4 at a predetermined speed in such a manner that the core wire material 3 unreeled from said winder 11 is fitted thereon, a cooling device 13 for water-cooling said inner layer tube 4 immediately after it is molded by said fore-stage extrusion molding device 12, thereby curing the same, and a braided layer attaching unit 14 for attaching said braided layer 5 to the outer surface of said inner layer tube 4 cooled by said cooling device 13, there by molding said braided tube 7. The inner and outer diameter dimensions of said inner layer tube 4 are constant in any cross section.

Said fore-stage extrusion molding device 12 includes an extruder 16 having a screw rotationally driven by an electric motor, and a die 17 having an inner layer tube molding passage to enable the resin extruded from the extruder 16 to forwardly pass therethrough, thereby making it possible to mold the inner layer tube 4.

Said catheter molding apparatus 1 includes a post-stage extrusion molding device 19 enabling said raw material tube 2 to be extrusion molded at a predetermined speed (m/min) by fitting said outer layer tube 8 of resin on said braided tube 7, a cooling device 20 for water-cooling said raw material tube 2 immediately after it is molded by said post-stage extrusion molding device 19, thereby curing the same, a take-off unit 21 for continuously taking off said raw material tube 2 cooled by said cooling device 20, and a winder 22 for winding the raw material tube 2 coming from said take-off unit 21.

Said winder 11, fore-stage extrusion molding device 12, cooling device 13, braided layer attaching unit 14, post-stage extrusion molding device 19, cooling device 20, take-off unit 21, and winder 22 are disposed continuously along the longitudinal direction of said tubes 4, 7, 8 and 2, respectively.

The respective maximum processing speeds (for example, 6-10 mm/min) of said fore-stage and post-stage extrusion molding devices 12 and 19 are set to be higher than the maximum processing speed (for example, 5 m/min) of said braided layer attaching unit 14. That is. The maximum processing speed of the catheter molding apparatus 1 coincides with the maximum processing speed of said braided layer attaching unit 14.

In FIGS. 1-5, said post-stage molding device 19 includes first and second extruders 29 and 30 for thermally melting first and second thermoplastic resins 26 and 27 and extrude them, and a die 34 having an inner layer portion molding passage 32 for causing said first resin 26 extruded from said first extruder 29 to pass forwardly therethrough to make it possible to mold the inner layer portion 8a of said outer layer tube 8, and an outer layer portion molding passage 33 for causing said second resin 27 extruded from said second extruder 30 to pass forwardly therethrough to make it possible to mold the outer layer portion 8b of said outer layer tube 8.

Said first and second resins 26 and 27 are of different kinds, differing in normal temperature hardness. Said first and second extruders 29 and 30 each have a screw driven by an electric motor.

Said inner and outer portion molding passages 32 and 33 are each in the form of a frustoconical sleeve tapering in going forward, and are disposed on the same axis 36. Further, radially of this axis 36, said inner layer portion molding passage 32 is positioned inwardly of the outer layer portion molding passage 33. The respective front ends of said inner and outer layer portion molding passages 32 and 33 serve as inner and outer extrusion ports 37 and 38. These inner and outer extrusion ports 37 and 38 are disposed close to each other radially of said axis 36.

A through-hole 39 of circular cross section passing through said axis 36 is molded in the die 34. Said through-hole 39 longitudinally passes through said die 34, enabling said braided tube 7 to pass forwardly through said through-hole 39.

Said die 34 has molded therein first and second inflow passages 40 and 41. These first and second inflow passages 40 and 41 enable the first and second resins 26 and 27 extruded from said first and second extruders 29 and 30 to individually flow into said inner and outer layer portion molding passages 32 and 33.

Said catheter molding apparatus 1 includes first and second flow regulating valves 43 and 44. These first and second flow regulating valves 43 and 44 include a valve case molded by said die 34, valve bodies 45 installed in the valve case (die 34) to enable the degrees of opening of said first and second inflow passages 40 and 41 to be adjusted, and actuators 46 enabling these valve bodies 45 to be individually opened and closed.

The first and second resins 26 and 27 flow from said first and second extruders 29 and 30, passing through said first and second inflow passages 40 and 41 toward said inner and outer layer portion molding passages 32 and 33. At this time, the opening and closing valve operation of the respective valve bodies 45 of said first and second flow regulating valves 43 and 44 enables individual adjustment of the flow rates Q1 and Q2 of said first and second resins 26 and 27 per unit time ($m^3$/min: hereinafter referred to simply as flow rates).

At the front surface of said die 34, an auxiliary die 48 is removably supported by a fastener 47. At a position forwardly remote from said inner and outer extrusion ports 37 and 38 and on said axis 36, an auxiliary die hole 49 is molded in said auxiliary die 48. Said inner and outer extrusion ports 37 and 38 communicate with said auxiliary die hole 49. Said raw material tube 2 is capable of forwardly passing through said auxiliary die hole 49. The raw material tube 2 and the auxiliary die hole 49 are the same in diameter dimension.

The outer region of an imaginary frustoconical sleeve 52 connecting the outer opening edger 50 of said outer extrusion port 38 to the opening edge 51 of said auxiliary die hole 49 has a space 53 molded throughout in the circumferential direction thereof. Although not shown, this space 53 communicates with the atmosphere side.

Figure 2:
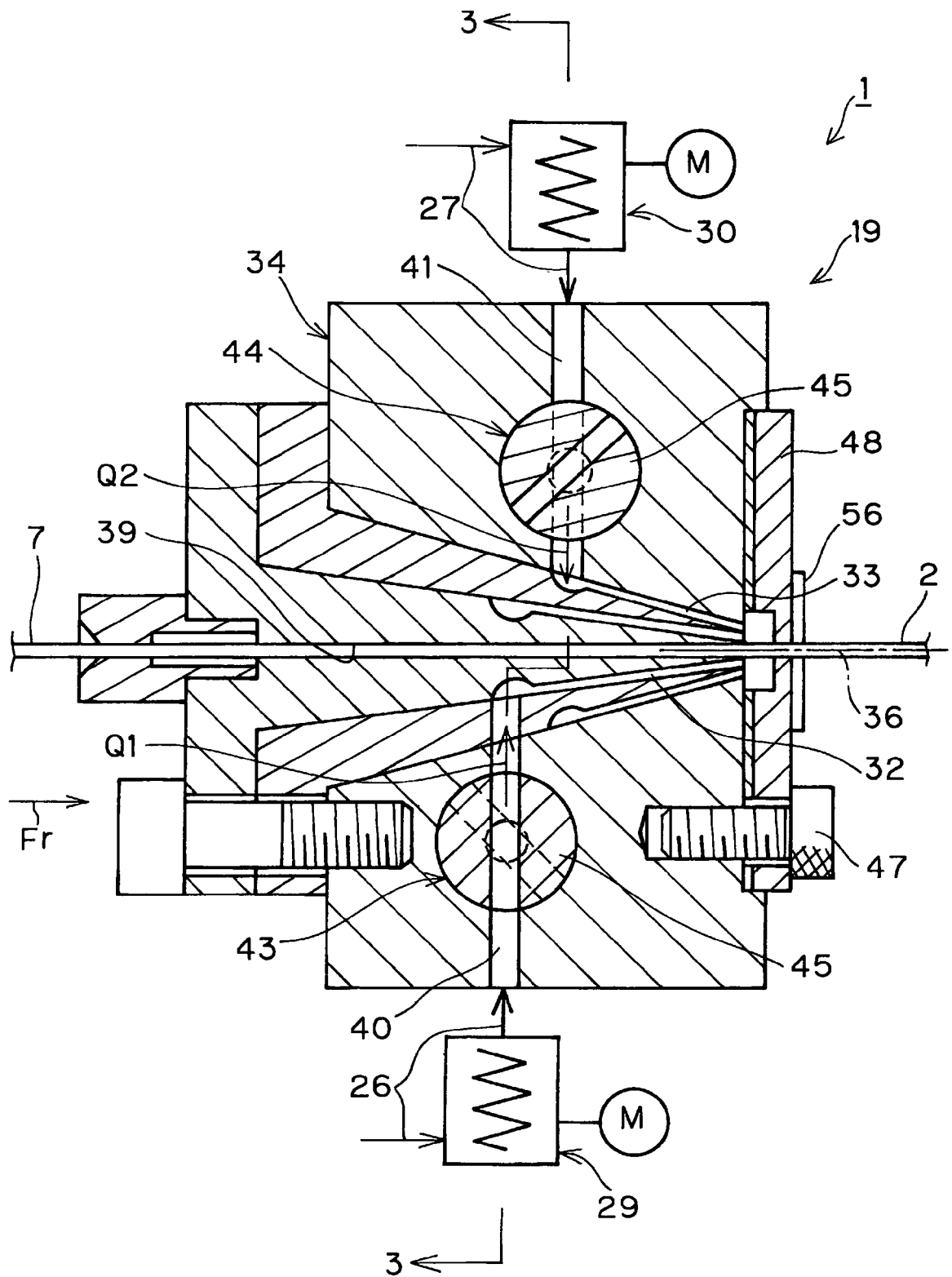
FIG. 2 is a sectional view of a post-stage extrusion molding device.
Figure 4:
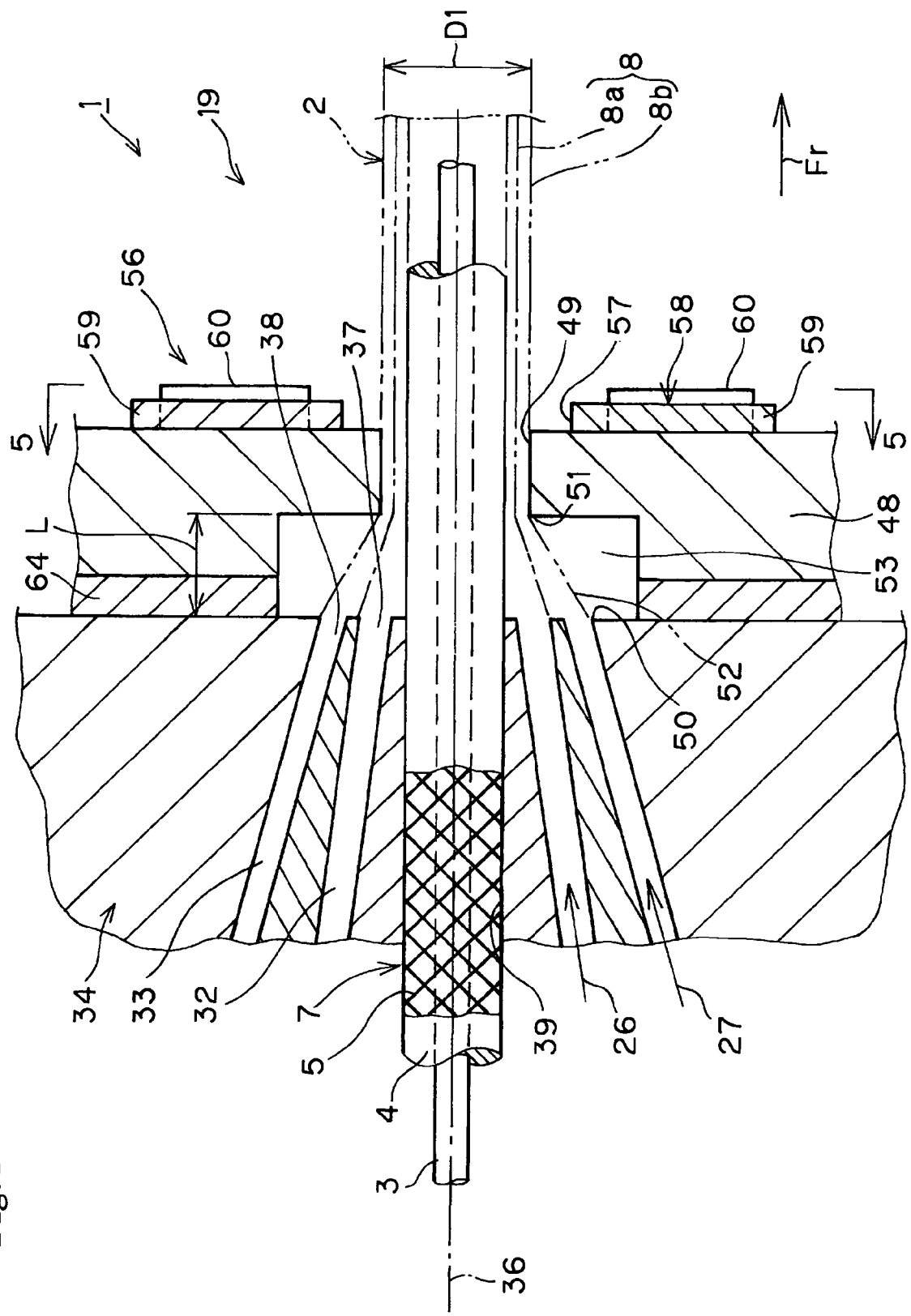
FIG. 4 is a partial enlarged view of FIG. 2.
Figure 5:
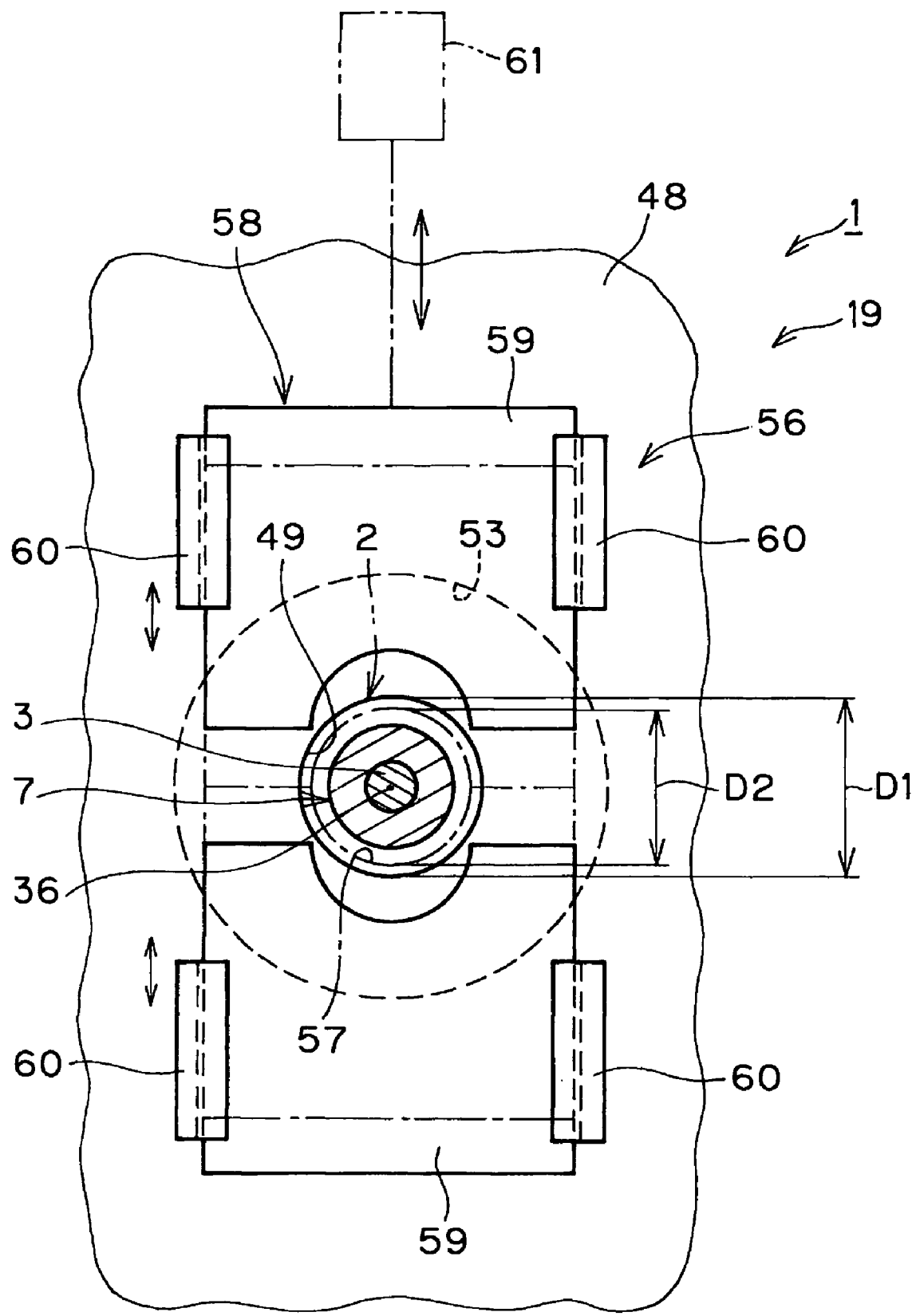
FIG. 5 is a view taken along the line 5-5 in FIG. 4.

In FIGS. 2, 4, and 5, an inner diameter varying device 56 is installed which enables the inner diameter dimension D1 of said auxiliary die hole 49 to be varied. This inner diameter varying device 56 includes a slide plate 58 having molded therein another auxiliary die hole 57 whose inner diameter dimension D2 is smaller than in said auxiliary die hole 49. This slide plate 58 is joined to the front surface of said die 34, and said another auxiliary die hole 57 is molded on said axis 36. Said slide plate 58 is vertically divided along the axis 36 of another auxiliary die hole 57, and is constituted by a pair of upper and lower split plates 59.

Guides 60 for guiding said two split plates 59 are attached to the front surface of said die 34. Said guides 60 guide said two split plates 59 in such a manner that they slide on the front surface of said die 34 and move toward and away from each other. Further, said inner diameter varying device 56 includes an actuator 61 adapted to move said split plates 59 in the manner described above.

In FIGS. 2, 4, and 5, in the direction of said axis 36, the separation distance dimension L from said inner and outer extrusion ports 37 and 38 to said auxiliary die hole 49 is variable. That is, adjusting plates 64 are removably interposed between the front surface of said die 34 and said auxiliary die 48. Said separation distance dimension L can be varied by changing the thickness or the number of said adjusting plates 64.

The respective electric motors of said fore-stage extrusion molding device 12, braided layer attaching unit 14, post-stage extrusion molding device 19, take-off unit 21, and winder 22 are variable in speed. That is, their processing speeds are variable. Said electric motors and actuators 46 and 61 are connected to an electronic controller. By this controller, said devices 12, 14, 19, 21, 22, 46, and 61 are feedback-controlled with a predetermined program, so that said raw material tube 2 is automatically molded.

In this case, the respective processing speeds of said fore-stage extrusion molding device 12, braided layer attaching unit 14, post-stage extrusion molding device 19, and winder 22 synchronize with the processing speed of said take-off unit 21.

The action of said catheter molding apparatus 1 to mold the raw material tube 2 will be described.

First, said fore-stage extrusion molding device 12, braided layer attaching unit 14, and wider 22 are driven. Further, said actuators 46 and 61 are rendered actuable. And, said fore-stage extrusion molding device 12 continuously extrusion molds said inner layer tube 4. Simultaneously therewith, said inner layer tube 4 is continuously taken off by said take-off unit 21.

The inner layer tube 4 immediately after it is molded by said fore-stage extrusion molding device 12 is once cooled by said cooling device 13. The driving of said braided layer attaching device 14 causes the braided layer 5 to be attached to the outer surface of said inner layer tube 4, so that said braided tube 7 is molded.

Next, the driving of the first and second extruders 29 and 30 of said post-stage extrusion molding device 19 causes the outer layer tube 8 to be integrally fitted on said braided tube 7, so that said raw material tube 2 is molded. Simultaneously therewith, said raw material tube 2 is continuously taken off by the take-off unit 21, and is wound by the winder 22.

The molding of said outer layer tube 8 will be described more concretely.

The first resin 26 extruded from said first extruder 29 passes through said first inflow passage 40 and first flow regulating valve 43, flowing into the rear of said inner layer portion molding passage 32. Next, said first resin 26 is passed through said inner layer portion molding passage 32 and extruded forwardly of said die 34. Thereby, said inner layer portion 8*a* is molded. Simultaneously therewith, this inner layer portion 8*a* is integrally fitted on said braided tube 7.

On the other hand, the second resin 27 extruded from said second extruder 30 passes through said second inflow passage 41 and second flow regulating valve 44, flowing into the rear of said outer layer portion molding passage 33. Next, said second resin 27 is passed through said outer layer portion molding passage 33 and extruded forwardly of said die 34. Thereby, said inner layer portion 8*b* is molded. Simultaneously therewith, this outer layer portion 8*b* is integrally fitted on said inner layer portion 8*a*.

Figure 3:
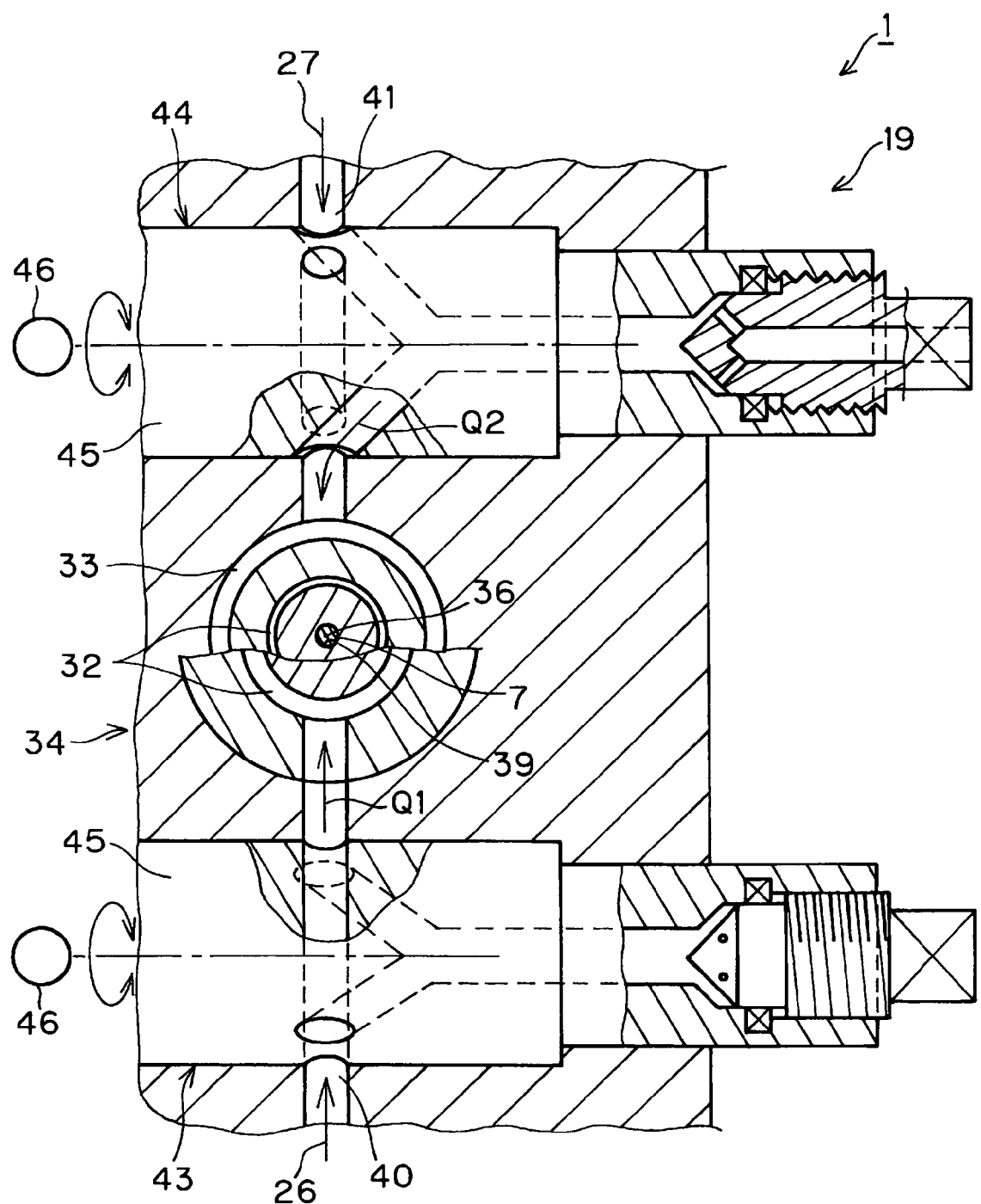
FIG. 3 is a sectional view taken along the line 3-3 in FIG. 2.

In FIGS. 1-6, during the molding of the raw material tube 2 by said catheter molding apparatus 1, the valve body 45 of the first flow regulating valve 43 is actuated by said actuator 46, as shown in FIGS. 2 and 3, for example, thereby increasing the degree of opening of the first inflow passage 40. On the other hand, the valve body 45 of said second flow regulating valve 44 is actuated to decrease the degree of opening of the second inflow passage 41. Thereupon, the flow rate Q1 of the first resin 26 moving from said first extruder 29 to the inner layer portion molding passage 32 increases. Further, the flow rate Q2 of the second resin 27 moving from said second extruder 30 to the outer layer portion molding passage 33 decreases.

Here, said first and second flow regulating valves 43 and 44 are so controlled that the total of said two flow rates Q1 and Q2 is constant. In this case, the respective extruded amounts of said first and second resins 26 and 27 from said first and second extruders 29 and 30 are constant. Further, the differences between the extruded amounts and said flow rates Q1 and Q2 are returned to the resin receiving sides of said first and second extruders 29 and 30 by said first and second flow regulating valves 43 and 44, respectively.

Figure 6:
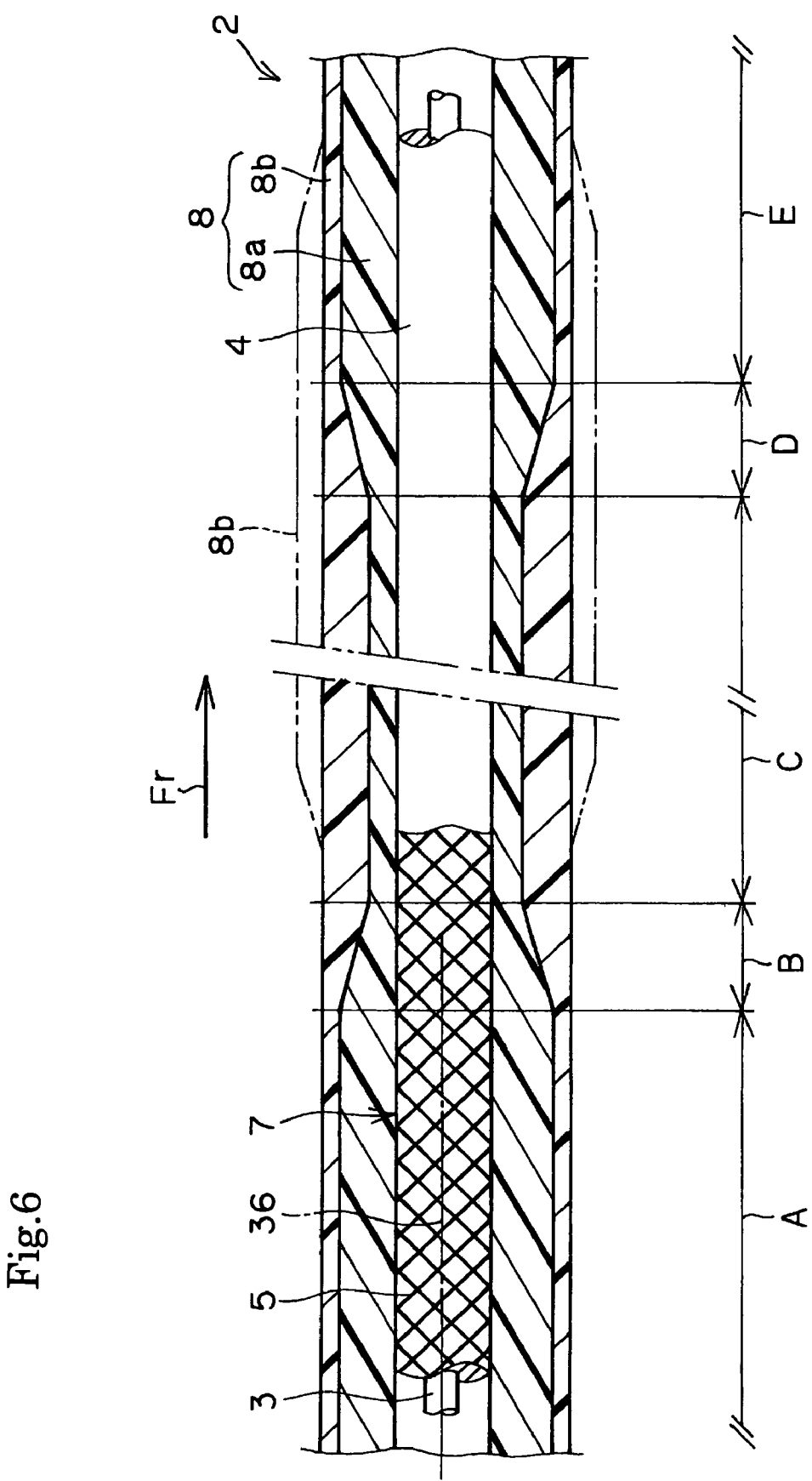
FIG. 6 is a sectional view of a raw material tube.

As described above, when the catheter molding apparatus 1 is operated, the raw material tube 2 molded by this catheter molding apparatus 1 has its outer diameter dimension made constant in any longitudinal portion, as shown in FIG. 6. Further, as shown at A and E in FIG. 6, the inner layer portion 8*a* of said outer layer tube 8 becomes thick-walled, while its outer layer portion 8*b* becomes thin-walled.

Conversely, the degree of opening of said first inflow passage 40 is decreased, while the degree of opening of said second inflow passage 41 is increased. Thereupon, by the action reverse to the above, the raw material tube 2, as shown at C in FIG. 6, assume a state in which the inner layer portion 8*a* of the outer layer tube 8 is thin-walled and the outer layer portion 8*b* is thick-walled.

Further, in the actuation of said first and second flow regulating valves 43 and 44, if they are switched such that the degree of opening of either said first inflow passage 40 or said second inflow passage 41 is increased and the other is decreased, then it takes some time to turn said valve body 45. Consequently, there form transition portions such that as shown at B and D in FIG. 5, the respective wall-thicknesses of the inner layer portion 8*a* and outer layer portion 8*b* of the outer layer tube 8 vary in the longitudinal direction.

On the other hand, as described above, when the outer layer portion 8*b* of the outer layer tube 8 is forwardly extruded from the outer extrusion port 38 of said outer layer portion molding passage 33, the outer surface of said outer layer portion 8b comes in contact with the air in said space 53, whereby it is cured to some extent. And, immediately after this curing, said raw material tube 2 is passed through said auxiliary die hole 49. At this time, the outer surface of the outer layer tube 8 of said raw material tube 2 slides while pressing the inner surface of said auxiliary die hole 49.

On the other hand, the actuation of said first and second flow regulating valves 43 and 44 increases the respective degrees of opening of the first and second inflow passages 40 and 41. Further, said inner diameter varying device 56 makes an adjustment such that the inner diameter dimension D2 of said auxiliary die hole 49 is increased. Thereupon, as shown in chain double-dashed lines in FIG. 6, the outer diameter dimension of said raw material tube 2 increases.

Here, the first resin 26 constituting the inner layer portion 8a of said outer layer tube 8 differs in hardness from the second resin 27 constituting the outer layer portion 8b. Consequently, as shown in FIG. 6, adjusting the respective wall-thicknesses and diameter dimensions of the inner and outer layer portions 8a and 8b in the outer layer tube 8 makes it possible to continuously and gradually change the hardness in any longitudinal portion of the raw material tube 2. Further, said adjustment of the wall-thickness and diameter dimension, as shown in FIG. 6, also makes it possible to continuously and gradually change the outer diameter dimension in any longitudinal portion of the raw material tube 2.

Thus, in the case of molding a catheter, first, the catheter molding apparatus 1 is operated for molding such that each portion of the raw material tube 2 meets the specifications of the catheter. Next, the raw material tube 2 is cut into portions of desired length in such a manner as to coincide with a catheter of desired specifications. Next, the core wire material 3 is extracted from said inner layer tube 4, whereby said catheter is molded.

FIG. 7 shows another embodiment concerning the raw material tube 2.

According to this embodiment, the degree of opening of said first inflow passage 40 is increased and the degree of opening of the second inflow passage 41 is decreased to total closure. Thereupon, as shown at A and E in FIG. 7, the outer layer tube 8 is composed of the inner layer portion 8a alone. On the other hand, the degree of opening of said first inflow passage 40 is decreased to total closure and the degree of opening of the second inflow passage 41 is increased. Thereupon, as shown at C in FIG. 7, the outer layer tube 8 is composed of the outer layer portion 8b alone.

The rest of the arrangement and function is the same as in said embodiment, so that a description thereof is omitted with the common reference characters entered in the drawing.

The above arrangement includes a fore-stage extrusion molding device 12 for extrusion molding said inner layer tube 4 of resin in such a manner that the core wire material 3 of metal is fitted thereon, a braided layer attaching unit 14 for attaching the braided layer 5 made by the molding of the reinforcing thread to the outer surface of the inner layer tube 4 molded by the fore-stage extrusion molding device 12 and once cooled, thereby molding said braided tube 7, a post-stage extrusion molding device 19 for extrusion molding the raw material tube. 2 for the catheter by fitting the outer layer tube 8 of resin on said braided tube 7, and a take-off unit 21 for taking off said raw material tube 2, said fore-stage extrusion molding device 12, braided layer attaching unit 14, post-stage extrusion molding device 19, and take-off unit 21 being disposed continuously along the longitudinal direction of said tubes 4, 7, 8, and 2.

Consequently, when said inner layer tube 4 is molded, its outer surface is cured to some extent by being once cooled. Thus, thereafter, when the braided layer 5 is attached to the outer surface of said inner layer tube 4, the reinforcing thread 6 of said braided layer 5 is prevented from cutting into the outer surface of said inner layer tube 4.

As a result, the accuracy of the outer diameter dimension of the braided tube 7 improves. Consequently, when the raw material tube 2 is molded by fitting the outer layer tube 8 on the braided tube 7, the accuracy of the outer diameter dimension of the raw material tube 2 improves. Thus, the dimensional accuracy of the catheter molded from the raw material tube 2 improves.

Further, as described above, the fore-stage extrusion molding device 12, braided layer attaching unit 14, post-stage extrusion molding device 19, and take-off unit 21 of the catheter molding apparatus 1 are continuously disposed. Consequently, as compared with the case of individually disposing them to discontinuously mold intermediate molded parts of the raw material tube 2, the arrangement of the catheter molding apparatus 1 becomes simple. That is, as described above, the molding of a catheter intended to improve dimensional accuracy is achieved by a simple arrangement.

Further, as described above, the respective maximum processing speeds of said fore-stage extrusion molding device 12, post-stage extrusion molding device 19, and take-off unit 21 are set to be greater than the maximum processing speed of said braided layer attaching unit 14.

Here, the improvement in the respective processing speeds of said fore-stage extrusion molding device 12, post-stage extrusion molding device 19, and take-off unit 21 can be achieved to some extent with a simple arrangement, for example, by simply increasing the speed of the electric motor. When it is intended to further increase the processing speed of said braided layer attaching unit 14, however, the centrifugal force in each arrangement rapidly increases, so that the arrangement will become relatively complicated.

So, as described above, the respective maximum processing speeds of said fore-stage extrusion molding device 12, post-stage extrusion molding device 19, and take-off unit 21 are set to be greater than the maximum processing speed of said braided layer attaching unit 14. That is, while the maximum processing speed of said braided layer attaching unit 14 is set at a desired value in such a way as not to make its arrangement excessively complicated, it is arranged that the maximum processing speed of the catheter molding apparatus 1 be not limited by the respective maximum processing speeds of said fore-stage extrusion molding device 12, post-stage extrusion molding device 19, and take-off unit 21. Thereby, the catheter molding apparatus 1 can rationally develop the maximum processing speed with a simple arrangement.

Further, as described above, the post-stage extrusion molding device 19 includes first and second extruders 29 and 30 for thermally melting and extruding first and second resins 26 and 27 of different kinds, a die 34 having molded therein an inner layer portion molding passage 32 for forwardly passing therethrough said first resin 26 extruded from said first extruder 29 to make it possible to mold the inner layer portion 8a of said outer layer tube 8 and an outer layer portion molding passage 33 for forwardly passing therethrough said second resin 27 extruded from said second extruder 30 to make it possible to mold the outer layer portion 8b of said outer layer tube 8, and first and second flow regulating valves 43 and 44 for making it possible to regulate the respective flow rates Q1 and Q2 per unit time of the first and second resins 26 and 27 extruded from said first and second extruders 29 and 30 and directed to said inner and outer layer portion molding passages 32 and 33.

Consequently, the molding of the outer layer tube 8 in said raw material tube 2 is achieved by causing the first and second resins 26 and 27 extruded by said first and second extruders 29 and 30 to pass through said inner and outer portion molding passages 32 and 33. Further, at this time, the respective flow rates of said first and second resins 26 and 27 are regulated by the actuation of said first and second flow regulating valves 43 and 44. Thereupon, the respective wall-thicknesses and outer diameter dimensions of the inner and outer layer portions 8a and 8b of said outer layer tube 8 can be adjusted to desired values to mold a desired raw material tube 2.

Here, when said first and second flow regulating valves 43 and 44 are actuated, the first and second resins 26 and 27 in the "passages" extending from said first and second flow regulating valves 43 and 44 to said inner and outer layer portion molding passages 32 and 33 are given external forces on the basis of this actuation, and their volumes tend to vary.

However, the volumes of the first and second resins 26 and 27 in said "passages" are smaller than said volumes from said first and second extruders 29 and 30 to said inner and outer layer portion molding passages 32 and 33. Consequently, as compared with the conventional art devoid of the first and second flow regulating valves, the volumetric changes, with respect to said external forces, of the first and second resins 26 and 27 in said "passages" are suppressed to be small.

Thus, the changes in the flow rates of the first and second resins 26 and 27 flowing through said inner and outer layer portion molding passages 32 and 33 follow the actuation of said first and second flow regulating valves 43 and 44 with good response. Consequently, the dimensional accuracy of the outer layer tube 8 of said raw material tube 2 improves. That is, the dimensional accuracy of the catheter improves.

Further, as described above, the respective valve bodies 45 of said first and second flow regulating valves 43 and 44 are disposed in said die 34.

Consequently, the volumes of the first and second resins 26 and 27 in said "passages" extending from the respective valve bodies 45 disposed in said die 34 to the inner and outer layer portion molding passages 32 and 33 formed in said die 34 become smaller. Thus, the volumetric changes, with respect to said external forces, of said first and second resins 26 and 27 in said "passages" are suppressed to be smaller.

As a result, the changes in the flow rates of the first and second resins 26 and 27 flowing through said inner and outer layer portion molding passages 32 and 33 follow the actuation of said first and second flow regulating valves 43 and 44 with better response. Consequently, the dimensional accuracy of the outer layer tube 8 of said raw material tube 2 further improves. That is, the dimensional accuracy of the catheter further improves.

Further, as described above, the respective front ends of the inner and outer layer portion molding passages 32 and 33 are used as inner and outer extrusion ports 37 and 38, an auxiliary die 48 is installed forwardly of said die 34, said auxiliary die 48 having an auxiliary die hole 49 molded therein which, at a position forwardly remote from said inner and outer extrusion ports 37 and 38, enables said raw material tube 2 to pass forwardly therethrough, and an imaginary frustoconical sleeve 52 which connects the outer opening edge 50 of said outer extrusion port 38 to the opening edge 51 of said auxiliary die hole 49 has a space 53 molded throughout its outer region in the circumferential direction thereof.

Consequently, in the molding of said raw material tube 2, when the outer layer tube 8 is extruded forwardly of the die 34, the outer surface of this outer layer tube 8 contacts the air in said space 53, whereby it is cured to some extent. And, immediately after this curing, the outer surface of said raw material tube 2 slides on the inner surface of said auxiliary die hole 49 while making pressure contact therewith. Thereupon, the outer surface of said raw material tube 2 is finished to be a smooth surface. Further, the outer diameter dimension of this raw material tube 2 is made to coincide with the inner diameter dimension of said auxiliary die hole 49 to have a desired dimension. As a result, the dimensional accuracy of the catheter further improves.

Further, as described above, the separation distance dimension L from the inner and outer extrusion ports 37 and 38 to said auxiliary die hole 49 is made variable.

Consequently, adjusting said separation distance dimension L makes it possible to adjust the time in which the outer surface of the outer layer tube 8 of the raw material tube 2 immediately after being extruded forwardly of said die 34 contacts the air in said space. Thereby, the extent of the curing of the outer surface of said outer layer tube 8 can be set in a more desirable state. And, since the outer surface of this outer layer tube 8 slides on the inner surface of said auxiliary die hole 49, the outer surface of the raw material tube 2 is finished to be a smoother surface. Further, the outer diameter dimension of this raw material tube 2 is made to be a more desired dimension.

In addition, the above is in accord with the illustrated examples. However, the cooling of the inner layer tube 4 molded by the fore-stage extrusion molding device 12 may be air-cooling rather than water cooling. Further, in the post-stage extrusion molding device 19, in addition to the first and second extruders 29 and 30, other extruders and an arrangement associated therewith may be installed.

Further, another slide plate may be superposed on said slide plate 58, which may be formed with auxiliary die holes different in inner diameter dimension from said auxiliary die holes 49 and 57. Further, inner diameter varying device 56 may have a construction similar to a camera shutter.

What is claimed is:

1. A catheter molding apparatus comprising:
    a fore-stage extrusion molding device for extrusion molding an inner layer tube of resin so as to fit a core wire material of metal therein;
    a braided layer attaching unit for attaching a braided layer made by the braiding of a reinforcing thread to the outer surface of the inner layer tube molded by said fore-stage extrusion molding device and once cooled, thereby molding a braided tube;
    a post-stage extrusion molding device for extrusion molding a raw material tube for a catheter by fitting an outer layer tube of resin on the braided tube; and
    a take-off unit for taking off said raw material tube,
    wherein said fore-stage extrusion molding device, braided layer attaching unit, post-stage extrusion molding device, and take-off unit are continuously disposed along the longitudinal direction of said tubes
    wherein said post-stage extrusion molding device includes first and second extruders for thermally melting and extruding first and second resins of different kinds, a die having molded therein an inner layer portion molding passage for forwardly passing there through said first resin extruded from said first extruder to make it possible to mold an inner layer portion of said outer layer tube and an outer layer portion molding passage for forwardly passing there through said second resin extruded from said second extruder to make it possible to mold an outer layer portion of said outer layer tube, and first and second flow regulating valves for making it possible to regulate the respective flow rates per unit time of the first and second resins extruded from said first and second extruders and directed to said inner and outer layer portion molding passages, and wherein the respective front ends of said inner and outer layer portion molding passages are used as inner and outer extrusion ports, an auxiliary die is installed forwardly of said die, said auxiliary die having an auxiliary die hole molded therein which, at a position forwardly remote from said inner and outer extrusion ports, enables said raw material tube to pass forwardly there through, and an imaginary frustoconical sleeve which connects an outer opening edge of said outer extrusion port to an opening edge of said auxiliary die hole has a space molded throughout its outer region in the circumferential direction thereof.

2. A catheter molding apparatus as set forth in claim 1, wherein the respective maximum processing speeds of said fore-stage extrusion molding device, post-stage extrusion molding device, and take-off unit are set to be greater than the maximum processing speed of said braided layer attaching unit.

3. A catheter molding apparatus as set forth in claim 1, wherein respective valve bodies of said first and second flow regulating valves are disposed in said die.

4. A catheter molding apparatus as set forth in claim 1, wherein the separation distance dimension from said inner and outer extrusion ports to said auxiliary die hole is made variable.

* * * * *